US008532763B2

(12) United States Patent
De Vos

(10) Patent No.: US 8,532,763 B2
(45) Date of Patent: Sep. 10, 2013

(54) CARDIOVERTOR/DEFIBRILLATOR

(75) Inventor: Gerrit Johannis De Vos, 's-Heerhendrikskinderen (NL)

(73) Assignee: Lisiak 1 B.V. (NL)

( * ) Notice: Subject to any disclaimer, the term of this patent is extended or adjusted under 35 U.S.C. 154(b) by 224 days.

(21) Appl. No.: 13/000,326

(22) PCT Filed: Jun. 18, 2009

(86) PCT No.: PCT/NL2009/050359
§ 371 (c)(1),
(2), (4) Date: Mar. 16, 2011

(87) PCT Pub. No.: WO2009/154459
PCT Pub. Date: Dec. 23, 2009

(65) Prior Publication Data
US 2011/0313480 A1    Dec. 22, 2011

(30) Foreign Application Priority Data
Jun. 18, 2008 (NL) .................................. 2001698

(51) Int. Cl.
*A61N 1/372* (2006.01)
(52) U.S. Cl.
USPC .................................................. 607/4
(58) Field of Classification Search
USPC .................................................. 607/4–5, 9
See application file for complete search history.

(56) References Cited

U.S. PATENT DOCUMENTS

| 4,088,138 | A | 5/1978 | Diack et al. |
| 4,969,468 | A | 11/1990 | Byers |
| 5,335,657 | A | 8/1994 | Terry, Jr. et al. |
| 5,514,175 | A | 5/1996 | Kim et al. |
| 5,571,148 | A | 11/1996 | Loeb et al. |
| 5,891,185 | A * | 4/1999 | Freed et al. ................ 607/72 |
| 5,957,956 | A | 9/1999 | Kroll et al. |
| 6,368,287 | B1 | 4/2002 | Hadas et al. |
| 6,603,654 | B2 * | 8/2003 | Rorvick et al. ............ 361/503 |
| 2003/0100930 | A1 | 5/2003 | Cohen et al. |
| 2003/0139781 | A1 | 7/2003 | Bradley et al. |
| 2003/0199945 | A1 | 10/2003 | Ciulla |

(Continued)

FOREIGN PATENT DOCUMENTS

| CA | 2507142 | 10/2006 |
| DE | 29716688 | 11/1997 |

(Continued)

OTHER PUBLICATIONS

Wang, et al., Clinical observation on effect of auricular acupoint pressing in treating sleep apnea syndrome, Jan. 2001, 3 pages.

(Continued)

*Primary Examiner* — Scott Getzow
*Assistant Examiner* — Amanda Patton
(74) *Attorney, Agent, or Firm* — Fliesler Meyer LLP

(57) ABSTRACT

Cardiovertor/defibrillator with electronics (12) that receives a detection signal from a detection device (16) indicating whether a heart of a mammal is fibrillating, processes the detection signal by running a program and generates a control signal for a stimulation device (17) based on the detection signal in order to allow the stimulation device (17) to provoke defibrillation of the heart by a resuscitating stimulation in the area of the pharynx of the mammal. The apparatus has a nose plug.

13 Claims, 4 Drawing Sheets

(56) References Cited

U.S. PATENT DOCUMENTS

| | | | |
|---|---|---|---|
| 2004/0176673 | A1 | 9/2004 | Wahlstrand et al. |
| 2004/0210261 | A1 | 10/2004 | King et al. |
| 2004/0243205 | A1 | 12/2004 | Keravel et al. |
| 2005/0281751 | A1 | 12/2005 | Levin |
| 2006/0020299 | A1 | 1/2006 | Shalev |
| 2006/0064139 | A1 | 3/2006 | Chung et al. |
| 2006/0149319 | A1 | 7/2006 | Kuo et al. |
| 2006/0173259 | A1 | 8/2006 | Flaherty et al. |
| 2006/0206162 | A1 | 9/2006 | Wahlstrand et al. |
| 2006/0217779 | A1 | 9/2006 | Ransbury et al. |
| 2007/0088404 | A1 | 4/2007 | Wyler et al. |
| 2007/0128420 | A1 | 6/2007 | Maghribi |
| 2007/0250145 | A1 | 10/2007 | Kraus et al. |
| 2007/0255379 | A1 | 11/2007 | Williams et al. |
| 2007/0255531 | A1 | 11/2007 | Drew |
| 2008/0103545 | A1 | 5/2008 | Bolea et al. |
| 2009/0240296 | A1* | 9/2009 | Zeijlemaker et al. ............. 607/5 |

FOREIGN PATENT DOCUMENTS

| | | |
|---|---|---|
| EP | 0404427 | 12/1990 |
| EP | 1790380 | 5/2007 |
| EP | 1825880 | 8/2007 |
| GB | 2220356 | 1/1990 |
| WO | 2004049937 | 6/2004 |
| WO | 2006108630 | 10/2006 |
| WO | 2006115877 | 11/2006 |
| WO | WO2006115877 | 11/2006 |
| WO | 2007003019 | 1/2007 |
| WO | 2007065083 | 6/2007 |
| WO | WO2007065083 | 6/2007 |
| WO | 2007146213 | 12/2007 |
| WO | 2007147046 | 12/2007 |
| WO | 2008072948 | 6/2008 |
| WO | 2008080062 | 7/2008 |
| WO | 2008157435 | 12/2008 |

OTHER PUBLICATIONS

Tomori, et al., Hypoxic apnoea induced by N2 inhalation can be reversed by the aspiration reflex in anaesthetized cats, Respiratory Medicine, Jan. 1991, pp. 61-65, vol. 85, Bailliere Tindall, London, GB.

Benacka, et al., The sniff-like aspiration reflex evoked by electrical stimulation of the nasopharynx, Respiration Physiology, Dec. 1995, pp. 163-174, vol. 102, Amsterdam, NL.

Janssens, et al., Respiratory and cardiac arrest under general anaesthesia: treatment by acupuncture of the nasal philtrum, The Veterinary Record, Sep. 22, 1979, pp. 273-276.

Tomori, et al., Reflex reversal of apnoeic episodes by electrical stimulation of upper airway in cats, Respiration Physiology, Dec. 1, 1995, pp. 175-185, vol. 102, No. 2-3.

Tomori, et al., Mechanisms and clinicophysiological implications of the sniff- and gasp-like aspiration reflex, Respiration Physiology, Oct. 1, 1998, pp. 83-98, vol. 114, No. 1.

Yu, et al., Mechanisms of effects of electrical stimulation of "Renzhong" (Du 26) on phrenic discharge in rabbits, Journal of West China University of Medical Sciences, Dec. 1989, pp. 384-388, vol. 20, No. 4.

Changa, et al., Decrease of anesthetics activity by electroacupuncture on Jen-Chung point in rabbits, Neuroscience Letters, Dec. 1, 1995, pp. 93-96, vol. 202, No. 1-2.

Hsu, et al., Shock resuscitation with acupuncture: case report, Emergency Medicine Journal, Mar. 1, 2006, 2 pages, vol. 23, No. 3.

Oleson, et al., Electroacupuncture and auricular electrical stimulation, IEEE Engineering in Medicine and Biology Magazine, Dec. 1, 1983, pp. 22-26, vol. 2, No. 4, IEEE Service Center, Pisacataway, NJ, US.

Miller, Oral and pharyngeal reflexes in the mammalian nervous system: their diverse range in complexity and the pivotal role of the tongue, Critical Reviews in Oral Biology & Medicine, Sep. 1, 2002, pp. 409-425, vol. 13, No. 5.

PCT International Search Report in connection with Application No. PCT/NL2009/050359 Dated Feb. 9, 2010, 6 pages.

PCT International Preliminary Report on Patentability in connection with Application No. PCT/NL2009/050359 Dated Oct. 5, 2010, 12 pages.

* cited by examiner

US 8,532,763 B2

CARDIOVERTOR/DEFIBRILLATOR

FIELD OF THE INVENTION

The invention relates to a cardioverter/defibrillator (CD).

BACKGROUND OF THE INVENTION

The brainstem contains a number of central mechanisms regulating a number of vital physiological functions. Disorders in the regulation of the cardio-pulmonary system can result in a number of pathological conditions some of which may be potentially life threatening.

Current CDs comprise one or more leads that, in use, are placed in a human heart. Removing such CD leads results in serious damage to the body, i.e., the heart, blood vessels and surrounding tissue. There is a need for CDs that do not show this disadvantage.

Research in cats has shown that breathing can be stopped by inhalation of anoxic mixtures for over 1 minute, with subsequently a severe drop in blood pressure and heart rate. Mechanical or electrical stimulation of the nasopharynx can induce a sniff- and gasp-like "aspiration reflex" (Tomori and Widdicombe, 1969, Beňačka & Tomori, 1995, Tomori et al. 1995, 1998, 2000). Due to resuscitation effects, the blood pressure returns to normal, heart rhythm normalizes, respiration and neuro-behavioral functions return to normal. The anesthetized cat seems to be in good condition, even after as long as three minutes without adequate blood pressure, heart rate and breathing. This experiment can be repeated over 10 times on the same cat, without any noticeable negative consequences.

Provocation of such an aspiration reflex has been indicated as a possible means for interruption of apnoea in cats (Tomori et al., 1991, 1995, Beňačka & Tomori, 1995, Jakus et al., 2004). Alternatively, similar resuscitation may be induced by (electro)-acupuncture, (electro)-acupressure or mechanical stimulation of the nasal philtre in cats, inducing spasmodic inspiration (Beňačka Tomori, 1997).

However, the current position of the published state of the art is that the typical spasmodic inspirations of the aspiration reflex provoked from the nasopharynx and oropharynx in cats are not notable in humans and in this latter species are superimposed by a strong vomiting reflex (Beňačka 2004).

Other researchers found reactions different from the aspiration reflex in humans in response to stimulation of the upper airways with high-frequency oscillating air pressure (Henke & Sullivan, 1992).

PCT/NL2006/000599, which has not been published prior to the priority date of the application relating to the present invention, describes the surprising discovery that a resuscitating stimulation of the brainstem with an induced aspiration reflex in order to obtain resuscitating physiological effects also works in human beings. That document also describes some devices designed for treating apnoea and related cardio-respiratory syndromes in humans via activation of the respiratory centre of the brainstem followed by an induced aspiration reflex. However, this document is silent as to possible application as a cardiovertor/defibrillator.

WO2006/115877 discloses an apparatus for stimulating the vagal nerve of a human being for treatment of atrial fibrillation.

SUMMARY OF THE INVENTION

The object of the present invention is to provide a method of defibrillation and an CD based on a resuscitating stimulation of the brainstem with an induced aspiration reflex via a stimulus to the pharyngeal area. Here, "CD" is to be understood as referring to a device that is capable to operate as at least one of a cardiovertor and a defibrillator.

To that end, the invention provides an CD as claimed in claim 1. Such an CD can advantageously be used in hospitals where patients in need of defibrillation may need help within a few minutes.

BRIEF DESCRIPTION OF THE DRAWINGS

The invention will be explained in detail with reference to some drawings that are only intended to show embodiments of the invention and not to limit the scope. The scope of the invention is defined in the annexed claims and by its technical equivalents.

DESCRIPTION OF EMBODIMENTS

The present invention, among others, relates to devices suitable for inducing autoresuscitation in a subject in need thereof. The term autoresuscitation should be understood to comprise resuscitation by activation of natural compensatory mechanisms of the human organism via inducing a sniff- and gasp-like aspiration reflex, or its alternative forms in various species, similar to that provided by means of spontaneous gasping autoresuscitation observed in non-human animals and human infants (Sridhar et al., 2003; Xie et al., 2004). When referring to induction of autoresuscitation in this specification the term resuscitation may be used. In the context of the present invention, subjects that may benefit from induction of autoresuscitation are subjects suffering from heart failures that can only be solved by an CD.

It is believed that the "aspiration reflex", via strong activation of the inspiratory centre, causes the controlling functions of the brainstem to be reset, similar to activation of brainstem centres during autoresuscitation induced by gasping. In rapid and strong inspiratory efforts during a gasp or a provoked aspiration reflex, activation of the inspiratory centre in the brainstem resets the failing centres of other vital functions, including the centres controlling the operation of the heart. This causes the centres in the brain controlling the operation of the heart to send a resetting signal to the heart. This signal may defibrillate the heart. This is quite surprising since, prior to filing of PCT/NL2002/000599, it was generally believed that a resuscitating stimulation of the brainstem with an induced aspiration reflex in order to obtain resuscitating physiological effects does not work in humans.

The inventor of the present invention has found that a pig in need of defibrillation could be defibrillated by a resuscitating stimulation in the area of the pharynx. The aspiration reflex due said resuscitating stimulation resulted in activation of the respiratory centre in the brainstem. This breathing centre is in contact with the cardiovascular control centre which was activated by the activation of the respiratory centre. This resulted in defibrillation of the pig's heart which is extremely surprising since it is believed that a pig's heart is very resistant against any form of defibrillation. In general, pigs will die after fibrillation of the heart.

A resuscitating stimulation in the area of the pharynx can induce defibrillation of a fibrillating heart in other mammals, like humans, too.

Figure 1:
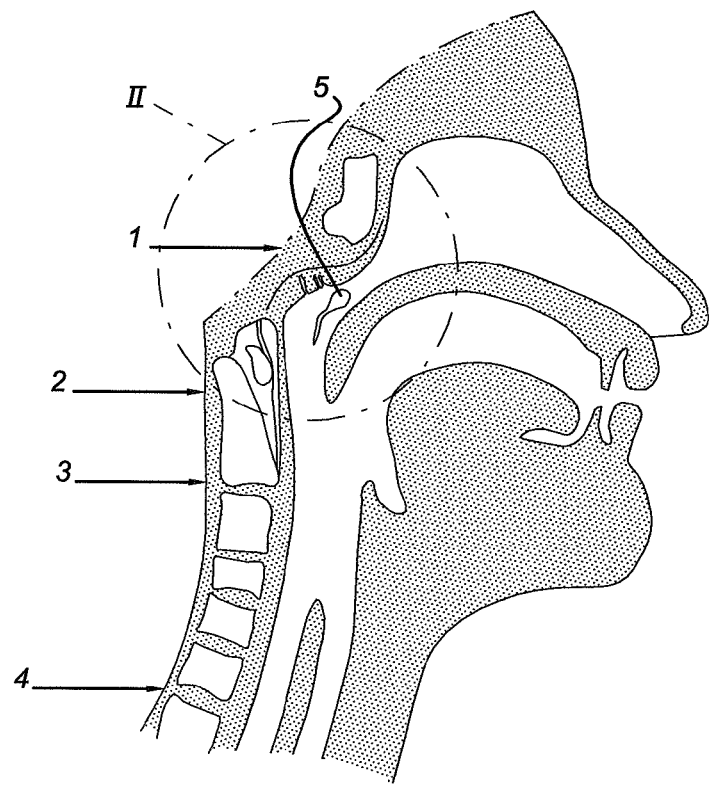
FIG. 1 is a schematic cross section of a part of the human head and neck.

As shown in FIG. 1 the pharynx of the human body is situated from the underside of the skull to the level of cervical vertebra C6. The pharynx may be divided in three compartments, the nasopharynx (roughly situated behind the nasal cavity between arrows 1 and 2), the oropharynx (roughly situated behind the oral cavity between arrows 2 and 3) and the laryngopharynx (roughly situated behind the larynx between arrows 3 and 4).

Figure 2:
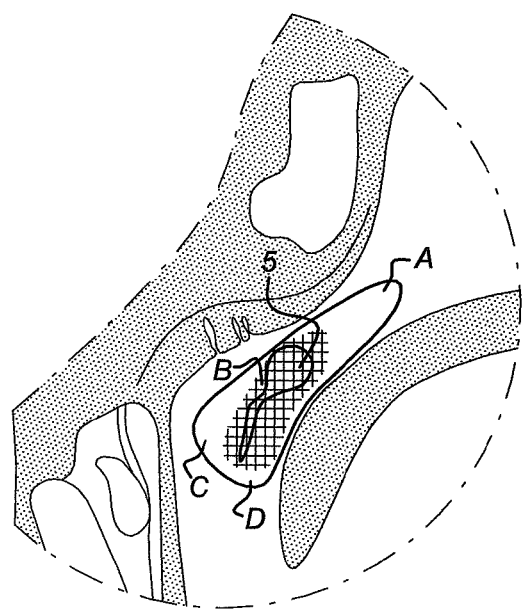
FIG. 2 is a detail from FIG. 1.

FIG. 2 shows the preferred location of resuscitating stimulation of the pharynx. Resuscitating stimulation is preferably administered in the area of the nasopharynx enclosed by reference marks A, B, C, D surrounding the tuba auditiva 5. More preferably resuscitating stimulation is administered in the direct proximity of the tuba auditiva 5 indicated by the hatched lines in FIG. 2.

Figure 3:
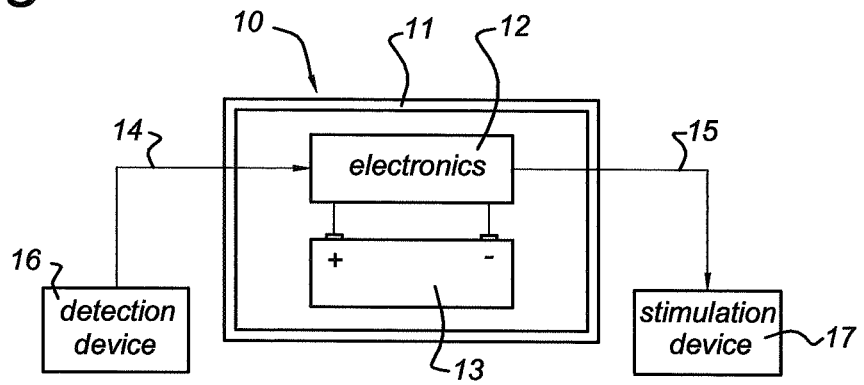
FIG. 3 shows a schematic block diagram of an electronic system according to the invention.

FIG. 3 shows an device 10 with a casing 11. Enclosed in the casing 11 is a battery 13 which is connected to electronics 12. The battery 13 may comprise lithium iodine with nanocrystaline cathode components, as generally used in cardiac pacemakers. The electronics 12 are connected to a detection device 16 via suitable wires 14, as well as to a stimulation device 17 via suitable wires 15.

The electronics 12 may be implemented by means of an analogue circuit, a digital circuit or a computer arrangement with a processor instructed by a suitable computer program, or any combination thereof. FIG. 2 shows an embodiment based on a computer arrangement.

Figure 4:
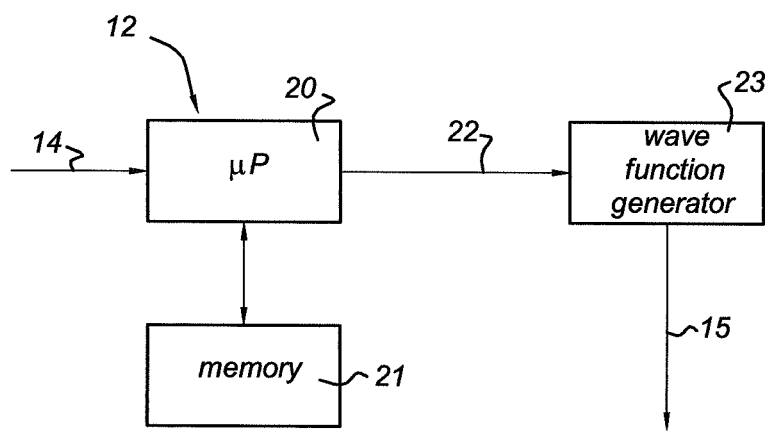
FIG. 4 shows an example of electronics that can be used in the present invention.

As shown in FIG. 4, the electronics 12 comprise a controller, e.g., in the form of a microprocessor 20 which is connected to a memory 21. Moreover, the microprocessor 20 is connected to a wave function generator 23 via suitable wires 22, which has an output connected to the wires 15 that are connectable to stimulation device 17.

The memory 21 may be implemented as several memory units of different types (RAM, ROM, etc.). The memory 21 stores instructions of a program to allow the microprocessor 20 to perform one or more functions. Optionally, memory 21 stores a number of detected parameter values as obtained from detection device 16. The memory 21 may be any suitable memory for storing a predetermined function such as a computer readable memory. The predetermined function may be a mathematical function or correlation. Suitable functions may be functions that are suitable for determining whether a determined parameter value is equal to, greater than or smaller than a predetermined threshold value. Based on his knowledge the skilled person will be able to determine suitable functions on the basis of which a response is required as a function of the determined parameter values. E.g. the function may relate the absence of certain parameter values below a certain threshold value to a certain time frame. Such a function may be determined to detect the presence of a fibrillating heart.

Based on the program as stored in the memory 21, the microprocessor 20 is able to process the number of detected parameter values as obtained from the detection device 16 in said function. For this, the detected parameter values are loaded into the microprocessor 20 either directly from the detection device 16 or alternatively from the memory 21 into which the detected parameter values were previously loaded. The function is loaded in the microprocessor 20 from the memory 21 or in an alternative embodiment the predetermined function may be embedded in said microprocessor 20. In the latter embodiment at least one memory is (partially) integrated in the microprocessor 20.

The detection device 16 may be any suitable device for detecting a number of parameter values. In the present specification, a "number" shall mean one or more unless explicitly stated otherwise. In use, the detection device 16 provides an output signal on wire 14, representing determined parameter values in response to determined parameter values. The determined parameter values are values of a parameter as measured/determined by the detection device 16 within a certain time frame. The parameter may be any parameter on the basis of which it may be determined whether a subject is in need of defibrillation.

Parameters suitable for determining whether a subject has a fibrillating heart and, thus, is in need of defibrillation include parameters relating to heartbeat or heart rate pattern. In principle, any location on the body to sense a fibrillating heart, for instance, via sensing the heartbeat and/or heart rate may be used by detection device 16. However, a suitable implementation is where the detection device 16 is arranged to sense blood flow in an artery, for instance, in the vicinity of the pharynx. Then, the detection device 16 transmits a blood flow signal to electronics 12. Microprocessor 20 is arranged to process the blood flow signal and generate an electrocardiogram from that in a way known to persons skilled in the art.

As is known to persons skilled in the art, measuring an electrocardiogram can be done on several location of a mammal body. Any such location can therefore be used in the context of the invention to establish whether the mammal has a fibrillating heart that needs to be defibrillated.

The stimulation device 17 is arranged to provide a response as a function of the number of processed parameter values. The stimulation device 17 may comprise a number of stimulation units designed to provide resuscitating stimulation in order to stimulate and/or reactivate the inspiratory centre of the brainstem. As indicated above, the stimulation and/or reactivation of the inspiratory centre as provided by the stimulation device 17 is in the pharynx. In the brainstem there are other controlling centres, such as the vasomotor centre and the neurons controlling cardiac activity, which will as a result also be influenced secondarily to the stimulation of the inspiratory centre.

Stimulation of certain locations distant from the brainstem, like in the pharynx, results in induction of resuscitation because in certain locations of the mammalian body afferent nerves connected to the inspiratory centre of the brainstem are present. Stimulation of such afferent nerves or their receptive zones results in activation of the inspiratory centre of the brainstem and through this in influencing of the other centres in the brainstem and other parts of the brain such that defibrillation may be induced.

It has been found that stimulation of the nasopharynx, more preferably the part of the nasopharynx in the proximity of the tubae auditivae, provides the strongest resuscitation effect with induction of the aspiration reflex.

The stimulation device 17 may be a mechanical, chemical or an electrical stimulation device. The electrical stimulation device may include a separate power source. A suitable power source may be an array of charged capacitors, allowing voltage selection for the stimulation, in case spikes are used. This separate power source may, alternatively, be absent in which case the stimulation device 17 will be connected to the battery 13 within casing 11 via wiring 15. The wave generator 23 as shown in FIG. 4 may be part of the stimulation device 17. In combination with such a power source, the wave generator 23 is arranged to produce a desired control signal for the stimulation device 17, for instance in the form of block waves, sinus waves or spikes of different length, frequency and amplitude, or combinations thereof.

In an embodiment, the stimulation units 43(i) are mechanical stimulation units arranged to provide a mechanical stimulus to the human body. Such mechanical stimulation units 43(i) may be formed by electrostriction components which produce a mechanical movement when excited by an electrical current. Such mechanical stimulation units 43(i) may have the form of needles.

The stimulation device 17 may further include or be connected to one or more stimulation electrodes for delivering an electrical stimulation to the pharynx. Such electrodes receive suitable stimulation signals based on the control signal received from the electronics 12. Electrodes may be monopolar or multipolar, including bipolar electrodes, and may be placed on the surface of or anchored in the pharynx. In the latter case, the electro-stimulation lead may be suitable to be anchored in the dorsolateral area of the nasopharynx. Alternatively, electrodes may have the form of needles arranged to at least partially penetrate the pharynx surface.

In an embodiment, the stimulation device 17 comprises a plurality of stimulation electrodes. By using a plurality of stimulation electrodes more complex stimulation currents can be provided to the body. This also provides the possibility of precise definition of the area to be stimulated. If a plurality of stimulation electrodes is used it is preferred that there is some distance between said electrodes. Due to this distance the electrical current will travel over that distance through the subject's body. This will enhance the stimulatory effect.

If spikes are used for the control signal, variations in the amplitude and duration of the spikes, i.e. the amount of energy can be made, apart from trains of spikes over an extended period of time (seconds) (Beňačka and Tomori, 1995). Sinus waves of various frequencies and duration, block waves, spikes, spike trains and any combination of these can be used. It is preferred to not just transfer energy, but to stimulate the targeted response centres more complexly to elicit the desired physiological response.

The CD according to the invention is, in an embodiment of the method of the invention, at least partly implanted in the pharyngeal area of a human body, i.e., at least casing 11 with its components inside. Preferably, in that embodiment, the CD is fully implanted in the pharyngeal area of the human body. Implantation is especially suitable when using electrical and/or mechanical stimulation means. Complete implantation of the device will make its use easier for the subject as there will be no parts on the surface of the subject's body. In an embodiment, the implantable CD is sized such that it's implantation in the pharyngeal area can be performed via a nostril or via a human throat.

From cardiac pacemakers it is known that the battery life can be as long as 10 years. With devices for resuscitating stimulation of the inspiratory neurons of the brainstem the battery life can be expected to be much longer, or the device can be made much smaller, as it does not have to stimulate as often as a cardiac pacemaker. In cardiac pacemakers, approximately 70% of the pacemaker's volume is taken up by the battery and connectors.

In one embodiment, the implantable device used in an embodiment of the method of the invention is arranged as shown in FIG. 3 where the casing 11 that accommodates electronics 12 and battery 13 is made of a flexible biocompatible material. A suitable material is silicone since that is found to be well tolerated by the human body. However, other flexible materials tolerated by the human body may be used instead.

The advantage of using a flexible casing is that it adapts itself to the form of the body where the casing is implanted. Thus, it does not, or hardly, perform any mechanical pressure to the human body after implantation, which would cause discomfort or even undesired stimulation by pressure.

In an embodiment, the flexible casing 11 is designed to be implantable in or behind the nasopharynx. Implanting such a casing can be done via the nose or mouth.

Figure 5:
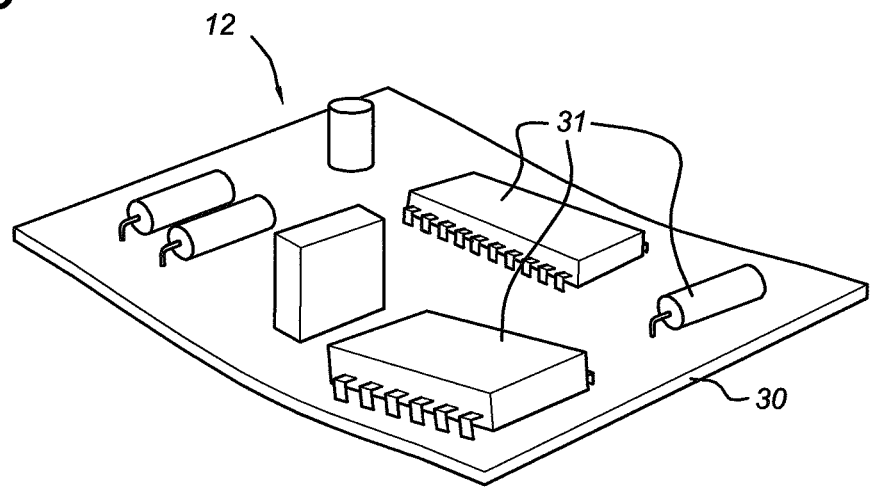
FIG. 5 shows a flexible substrate with some electronic components on top of it.

In such an embodiment, the battery may be made flexible too. Alternatively, the battery may consist of two ore more small batteries yielding a flexible battery pack. The electronics 12 may be made of flexible components as well or at least electronic components may be provided on a flexible substrate, e.g., a flexible printed circuit board. FIG. 5 shows such a flexible substrate 30 having electronic components 31 located on at least one surface. The stimulation device 17 may be located inside the casing 11 too and be made of electronic components on a flexible substrate too. Then, the stimulation device 17 may be arranged as shown in FIG. 5 as well. The electronic components of the electronics 12 may be arranged on a first flexible substrate and the stimulation device 17 may be arranged on a second flexible substrate. However, these first and second substrates may be a single substrate. The battery 13 may be provided on that substrate too. The detection device 16 may be located inside the casing 11 too and be made of electronic components on a third flexible substrate too. Then, the detection device 16 may be arranged as shown in FIG. 5 as well. The substrates with the electronic components of the electronics 12, the detection device 16 and the stimulation device 17 may be separate substrates. Alternatively, however, they may be one single substrate.

Figure 6:
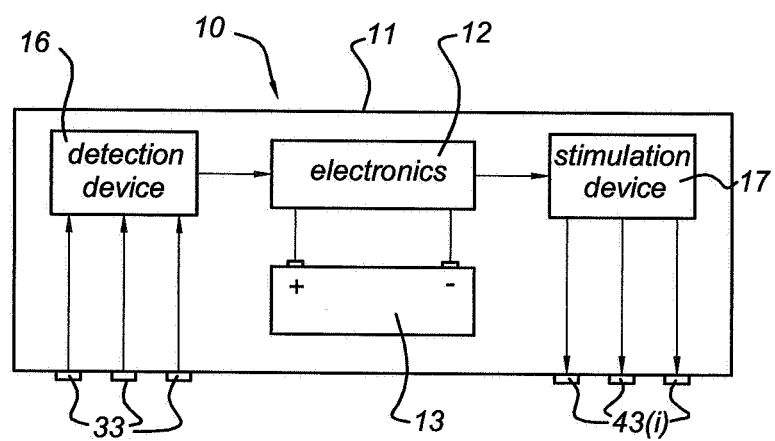
FIG. 6 shows a different embodiment of the invention.

An implantable device 10 used in the invention may be designed such that it does not comprise any external detection or stimulation leads. As shown in FIG. 6, the casing 11 of such a device 10, then, accommodates all components including the detection device 16, the electronics 12, the battery 13 and the stimulation device 17. The battery 13 is shown to be connected to the electronics 12 but may equally well be connected to the detection device 16 and the stimulation device 17. Then, the casing 11 may be partly conductive. For instance, the casing 11 may be provided with conductive pads 33 connected to the detection device 16 and operating as a voltage sensitive matrix for the detection of an ECG. Then, the voltage sensitive pads are connected to suitable filters and amplifiers to render such an ECG, as will be evident to persons skilled in the art. The conductive casing 11 may similarly be provided with electrical pads 43(i), i=1, 2, 3, . . . , I connected to the stimulation device 17 which are used to guide an electric stimulation current to the pharynx of the body in its direct proximity. Electrical pads 33, 43(i) may be made by making the casing 11 from silicone and doping portions thereof with a suitable metal like titan or platina. Such doped portions, then, form the electrical pads 33, 43(i). Electrical pads may be made from any suitable metal, such as titanium or platinum, possibly embedded in or arranged on the (silicone) casing 11.

Figure 7:
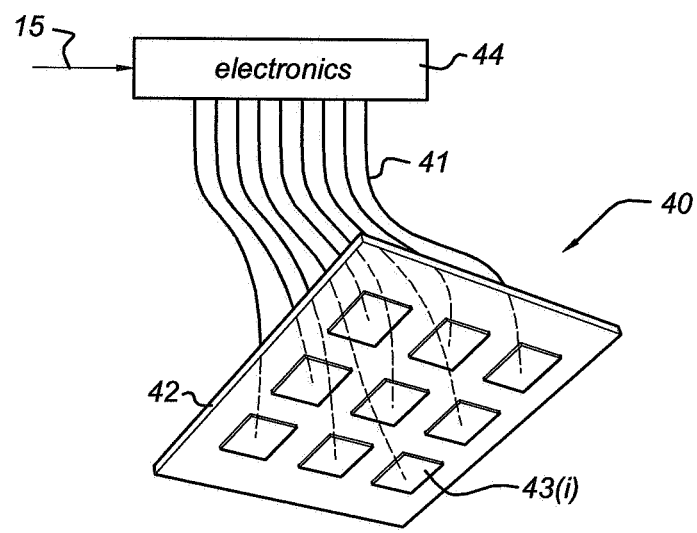
FIG. 7 shows a substrate with a matrix arrangement of stimulation units.

The pads 43(i) may be formed as a two dimensional stimulation matrix 40. FIG. 7 shows such a stimulation matrix 40 that can be used in the device of the invention. As shown in FIG. 7, the stimulation matrix 40 has a substrate 42 provided with a plurality of stimulation units 43(i) arranged in a two dimensional pattern. Substrate 42 may be part of the casing 11 or be provided as a separate unit outside casing 11. The stimulation units 43(i) are arranged in a matrix form. The arrangement shown comprises stimulation units 43(i) in a regular matrix pattern. However, the invention is not restricted to this arrangement. Other regular patterns or irregular patterns may be used instead.

In a further alternative embodiment, only the stimulation device 17 is located inside casing 11 and the stimulation units 43(i) are located on the casing 11 whereas detection circuit 16 is located outside casing 11 like in the arrangement shown in FIG. 3.

Casing 11 may be made from a conducting material like titan or platina. In such a case, when the stimulation units 43(i) themselves are conductive too they should be electrically isolated from the conductive casing 11. This can be done in any way known to a person skilled in the art.

Such an implantable device can be made auto-optimizing. The electronics 12 can be arranged to perform an impedance measurement on predetermined locations on the skin to locate one or more optimal stimulation points, i.e., points where an aspiration reflex can be induced best. Such an impedance measurement can be performed by using the stimulation matrix and measuring impedance levels of the skin between several stimulation units 43(i). This renders a 2D pattern of impedance levels of the measured area on the skin. Areas with a lower impedance may be better points for providing the stimulus.

The electronics 12 can be arranged to send different types of stimulation signals to the stimulation units 43(i), either in form or in amplitude or both. The effect of the different stimulation signals per stimulation unit 43(i) can be measured by detection device 16 and be evaluated by electronics 12. Electronics 12 can be programmed to amend these stimulation signals by amending its control signal as output to the stimulation device 17.

Moreover, the electronics 12 can be programmed to randomly vary its generated control signal such that the stimulation signals produce random stimuli over the area of the body stimulated by the stimulation units 43(i). This could reduce adaptation of the body to the generated stimuli and, thus, enhance efficiency of the device 10.

Figure 8A:
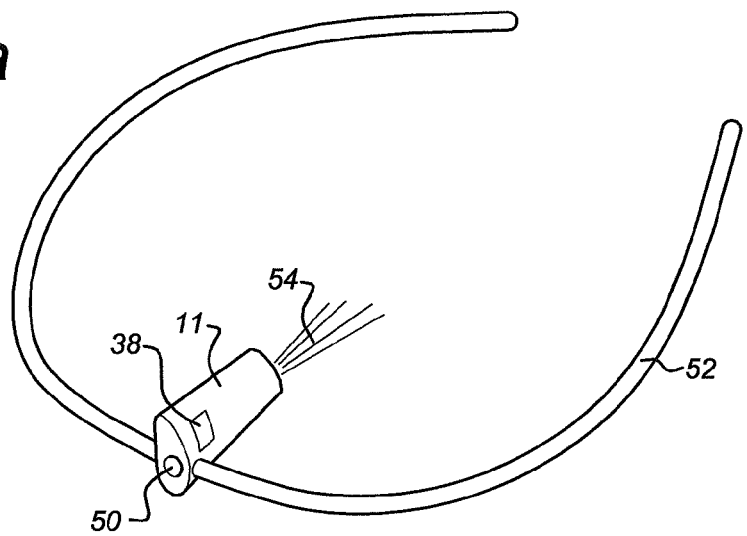
FIGS. 8a, 8b, and 8c show embodiments of an apparatus according to the invention.
Figure 8B:
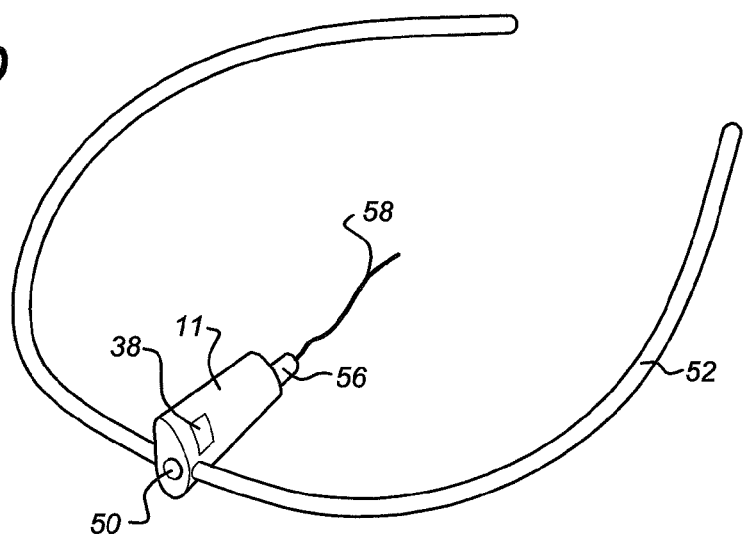
Figure 8C:
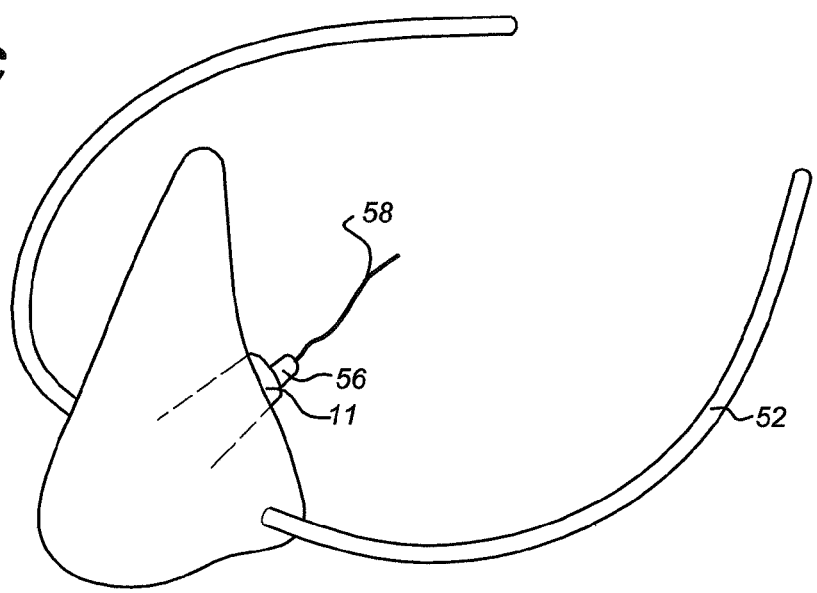

FIGS. 8a, 8b and 8c show advantageous embodiments of an apparatus according to the invention. The method of the invention can also be applied with the embodiments of these figures.

The apparatus as shown in FIG. 8a comprises casing 11 which is designed as a nose plug formed so as to allow to be inserted into a human nostril. Preferably, the casing 11 is flexible so as to fit easily. The casing 11 comprises a through hole 50 designed such that it allows the user to breath through the through hole 50. The casing may comprise detection device 16 internally such that it can measure any breathing activity by measuring the airflow through the through hole 50. Such a detection by detection device 16 may be based on any physical principle like flow measurement, temperature measurement, pressure measurement, etc.

In addition to the internal detection device 16, the system may comprise one or more sensors 38 located on the outside of the casing 11 and arranged to detect a heartbeat signal from an artery in the nose. Such a sensor may be based on measuring sound or a pressure. The casing 11 is connected to holding unit like a brace or bracket 52 to be worn on a human head and arranged to keep the nose plug shaped casing 11 in the nostril when it is in use.

In the embodiment of FIG. 8a, the casing 11 comprises stimulation device 17 too which is arranged to provide a spray 54 of a chemical composition into the nostril. The chemical stimulation may be induced by contacting the upper airways with a chemical composition inducing resuscitation. The chemical composition at the time of contacting with the pharynx is preferably in a gas or 10 aerosol form. Many odors are the result of a mixture of chemical compounds. Chemical induction of resuscitation may be provided by trigemino-olfactoric stimulants comprising for example one or more of vanillin, amylacetate, propionic acid or 15 phenylethylalcohol. However, it is explicitly stated that the present invention is not restricted to chemical stimulation with these odors/compounds.

For distributing the chemical composition the stimulation device 17 may comprise a spraying unit. The spraying unit may be suitable for spraying a (pressurized) gas and/or spraying (including nebulising) a liquid. Suitable spraying units are known to the skilled person.

FIG. 8b shows an alternative embodiment of an apparatus according to the invention. Components with the same reference numbers refer to the same components as in FIG. 6a. However, the apparatus of FIG. 6b is arranged to provide at least one of an electrical and a mechanical stimulus to the pharyngeal area. To that end, the casing 11 is provided with a tube 56 through which at least one of a thread, a wire and a fibre 58 extends. The length of the thread, a wire and a fibre 58 is such that it touches the pharyngeal area once the casing 11 is inserted into a nostril. The thread, wire or fibre may be connected to a suitable motor (not shown) and arranged to stimulate the nasopharyngeal area by a suitable mechanical movement as instructed by electronics 12. Alternatively, the wire 58 may be connected to electronics 44 within stimulation device 17 arranged to provide electrical stimulation signals to the wire 58 as instructed by electronics 12.

FIG. 8c shows an embodiment in which the casing 11 is connected to a nose piece 60 that can be shifted over a human nose. The nose piece 60 is connected to brace or bracket 52.

Although the present invention has been explained with reference to a method and an apparatus to counteract a fibrillating heart, it should be understood that the same apparatus can be used to counteract other disorders of a body like a heart infarct or a brain infarct. A heart infarct can be detected by using a detector device 16 that is arranged to measure an ECG signal. A heart infarct can, for instance, be detected from measuring the QRS complex as is known to persons skilled in the art. If a heart infarct is detected, the apparatus can be used to stimulate a pharyngeal area to generate a resuscitating stimulation in order to activate the respiratory centre in the brainstem and, in turn, activate the cardiovascular control centre.

A brain infarct, a TIA or an epileptic attack can be counteracted in a similar way. Moreover, the damages can be better controlled. If a subject is suspected of suffering from a brain infarct an embodiment of the apparatus and method of the invention can be used in which the detection device 16 is arranged to perform a CT scan or MRI scan allowing the electronics 12 to determine whether the subject has a brain infarct. This is necessary to be sure that the subject concerned is not suffering from for instance a brain haemorrhage which may result in similar disfunctionings of the body but where the proposed treatment probably does not work.

It should be understood that the embodiments presented in the examples above are solely intended to illustrate the present invention and are not intended to limit the scope of the invention which is only limited by the annexed claims and its technical equivalents.

REFERENCES

Arita H., Oshima T., Kita I., Sakamoto M.: Generation of hiccup by electrical stimulation in medulla of cats. Neurosci. Lett. 175: 67-70, 1994.

Batsel H. L., Lines A. J.: Bulbar respiratory neurons participating in the sniff reflex in the cat, J. Exper. Neurol 39:469-481,1973

R. Beňačka, Disorders of central regulation of breathing and their influencing by upper airway reflexes (in Slovak). Orbis Medince S; No.: 53-63, 2004, R. Beňačka and Z. Tomori, The sniff-like aspiration reflex evoked by electrical stimulation of the nasopharynx, Respir. Physiol. 102: 163-174, 1995.

J. Jakuš, Z. Tomori and A. Stransky, Neural determinants of breathing, coughing and related motor behaviours, Monograph, Wist, Martin, 2004.

Sridhar R., Thach B. T. et al.: Characterization of successful and failed autoresuscitation in human infants including those dying of SIDS. Pediatr. Pulmon. 36:113-122, 2003.

St John W. M., Bledsoe T. A., Sokol H. W: Identification of medullary loci critical for neurogenesis of gasping J. Appl. Physiol. 56: 1008-1019, 1984.

Z. Tomori, M. Kurpas, V. Doni. and R. BeÁa.ka, Reflex reversal of apnoeic episodes by electrical stimulation of upper airway in cats, Respir. Physiol. 102: 175-185, 1995.

Z. Tomori, R. Beňačka, V. Doni. and J. Jakuš, Contribution of upper airway reflexes to apnoea reversal, arousal, and resuscitation, Monaldi Arch. Chest Dis. 55: 398-403, 2000.

Z. Tomori, R. Beňačka and V. Doni., Mechanisms and clinicophysiological implications of the sniff- and gasp-like aspiration reflex, Respir. Physiol. 114: 83-98, 1998.

Z. Tomori and J. G. Widdicombe, Muscular, bronchomotor and cardiovascular reflexes elicited by mechanical stimulation of the respiratory tract, J. Physiol 200: 25-49, 1969.

Xie J., Weil M. H., Sun S., Yu T., Yang W.: Spontaneous gasping generates cardiac output during cardiac arrest, Crit. Care Med. 32: 238-240, 2004.

The invention claimed is:

1. A cardiovertor/defibrillator comprising:
a casing;
electronics arranged within said casing;
a detection device connected to said electronics;
a stimulation device connected to said electronics; and
the electronics being arranged to receive a detection signal from said detection device indicating a disorder of a body including at least one of a fibrillating heart and a heart infarct to process said detection signal and to generate a control signal for said stimulation device based on said detection signal in order to allow said stimulation device to generate a resuscitating stimulation in order to activate the respiratory centre in the brainstem and, in turn, counteract said disorder, the casing being designed as a nose plug arranged to be inserted into a nostril, and the stimulation device being arranged to stimulate a nasopharyngeal area of said mammal, the cardiovertor/defibrillator either:
being designed such that the stimulating device comprises a spraying unit for distributing a chemical composition into the nostril, or
being designed such that it comprises a thread, wire or fibre having a length such that it touches the pharyngeal area once the casing is inserted into the nostril, which thread, wire or fibre is connected to a motor and arranged to stimulate the nasopharyngeal area by a suitable mechanical movement as instructed by said electronics, or
being designed such that it comprises a wire having a length such that it touches the pharyngeal area once the casing is inserted into the nostril, which wire is arranged to provide electrical stimulation signals to said wire as instructed by said electronics.

2. The cardiovertor/defibrillator according to claim 1, wherein said cardiovertor/defibrillator comprises a nose cap connected to said casing.

3. The cardiovertor/defibrillator according to claim 1, wherein said casing is made of a flexible biocompatible material.

4. The cardiovertor/defibrillator according to claim 3, wherein said flexible material is silicone.

5. The cardiovertor/defibrillator according to claim 4, wherein said electronics comprise electronic components on a flexible substrate.

6. The cardiovertor/defibrillator according to claim 1, wherein said electronics comprise a microprocessor connected to a wave function generator, the wave function generator being arranged to produce said control signal having a wave form selected from at least one of a sinus wave, block wave, spike train or any combination thereof with a predetermined frequency, duration and amplitude.

7. The cardiovertor/defibrillator according to claim 1, wherein said detection device comprises a sensor on said casing for sensing a heartbeat signal.

8. The cardiovertor/defibrillator according to claim 1, wherein said casing comprises a through hole to allow said mammal to breath through said nostril.

9. The cardiovertor/defibrillator according to claim 8, wherein said detection device is arranged to sense breathing activity from air flow through said through hole.

10. Cardiovertor/defibrillator according to claim 1, wherein said cardiovertor/defibrillator comprises a plurality of electrodes to contact said nasopharynx and having some distance between them, such as to cause an electrical current to flow over said distance through said nasopharynx.

11. Cardiovertor/defibrillator according to claim 1, said chemical composition comprises trigemino-olfactoric stimulants comprising one or more of vanillin, amylacetate, propionic acid and phenylethylalcohol.

12. A method of counteracting a disorder of a body comprising:
detecting whether said body shows said disorder of a body including at least one of a fibrillating heart and a heart infarct;
generating a resuscitating stimulation in order to activate the respiratory centre in the brainstem and, in turn, activate the cardiovascular control centre and thus to counteract said disorder; and
wherein said resuscitating stimulation is applied to a nasopharyngeal area of said mammal.

13. The method according to claim 12, comprising implanting an implantable cardiovertor/defibrillator in or behind the nasopharynx in said mammal, which is designed to perform said detecting and said generating.

* * * * *